US00PP26648P2

(12) United States Plant Patent
Zaiger et al.

(10) Patent No.: US PP26,648 P2
(45) Date of Patent: Apr. 26, 2016

(54) NECTARINE TREE NAMED 'REED'

(50) Latin Name: ***Prunus persica* var. *nucipersica***
Varietal Denomination: Reed

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 19 days.

(21) Appl. No.: 14/121,977

(22) Filed: Nov. 10, 2014

(51) Int. Cl.
*A01H 5/08* (2006.01)

(52) U.S. Cl.
USPC ..... Plt./190

(58) Field of Classification Search
USPC ..... Plt./190
CPC ..... A01H 5/0856
See application file for complete search history.

*Primary Examiner* — Kent L Bell

(57) ABSTRACT

A new and distinct variety of nectarine tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous, upright growth.
2. Regular and productive bearer of medium to large size fruit.
3. Fruit with firm, yellow flesh.
4. Fruit ripening in the early maturity season.
5. Fruit with an attractive dark red skin color.

1 Drawing Sheet

Botanical designation: *Prunus persica* var. *nucipersica*.
Variety denomination: 'Reed'.

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of nectarine tree was originated and asexually reproduced by us in our experimental orchard located near Modesto, Stanislaus County, Calif.

2. Prior Varieties

Among the existing varieties of nectarine trees, which are known to us, and mentioned herein, 'Honey May' Nectarine (U.S. Plant Pat. No. 19,363), 'Zee Fire' Nectarine (U.S. Plant Pat. No. 13,501) and our proprietary non-patented nectarine seedling selections '53ZH604', '63MA126', '2LG339' and '213LP106'.

STATEMENT REGARDING FEDERALLY SPONSORED RESEARCH AND DEVELOPMENT

Not applicable.

ORIGIN OF THE VARIETY

The new and distinct variety of nectarine tree (*Prunus persica* var. *nucipersica*) was originated by us in our experimental orchard located near Modesto, Calif. from seed of a first generation cross between 'Honey May' Nectarine (U.S. Plant Pat. No. 19,363) and our proprietary non-patented nectarine seedling selection with the field identification number '53ZH604'. The non-patented nectarine pollen parent (53ZH604) originated as an open pollinated seedling selection from our proprietary non-patented nectarine seedling '63MA126' which is from seed of a first generation cross between our proprietary non-patented nectarine seedling selections '2LG339' and '213LP106'. A large number of these first generation seedlings were budded onto older established trees of 'Nemaguard' Rootstock (non-patented) to enhance earlier fruit production. Under close and careful observation we recognized the present budded seedling exhibited desirable fruit and tree characteristics and was selected in 2010 for additional asexual propagation and commercialization.

ASEXUAL REPRODUCTION OF THE VARIETY

In 2010 asexual reproduction of the new and distinct variety of nectarine tree was by budding to 'Nemaguard' Rootstock (non-patented), as performed by us in our experimental orchard located near the original tree and all characteristics of the tree and its fruit are established and transmitted through succeeding asexual propagations.

SUMMARY OF THE NEW VARIETY

The present new variety of nectarine tree (*Prunus persica* var. *nucipersica*) is of large size, vigorous, upright growth and is a regular and productive bearer of medium to large size fruit with a low winter chilling requirement of 300 hours. The fruit is further characterized by its firm, yellow flesh, having an attractive dark red skin color with good flavor and eating quality. In comparison to its seed parent 'Honey May' Nectarine (U.S. Plant Pat. No. 19,363) the fruit of the new variety is approximately 10 days later in maturity. In comparison to its proprietary non-patented pollen parent '53ZH604' nectarine the fruit of the new variety is approximately 7 days later in maturity. In comparison to the commercial variety 'Zee Fire' Nectarine (U.S. Plant Pat. No. 13,501) the fruit of the new variety has a more attractive dark red skin color and is approximately 9 days earlier in maturity.

DESCRIPTION OF THE PHOTOGRAPH

The accompanying color photographic illustration shows typical specimens of the foliage and fruit of the present new nectarine variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 6 year old tree and the colors are as nearly true as is reasonably possible in a color representation of this type.

DESCRIPTION OF THE VARIETY

The following is a detailed botanical description of the new variety of nectarine tree, its flowers, foliage and fruit, as based on observations of 6 year old specimens grown near Modesto, Calif., with color in accordance with Munsell Book of Color published in 1958.

Tree:

*Size*.—Large, usually pruned to 3 to 3.5 meters in height and width for economical harvesting of fruit, varies with different cultural practices.

*Vigor*.—Vigorous, growth of 1.5 to 2 meters in height the first growing season. Varies with soil type, fertility of soil and climatic conditions.

*Form*.—Upright, usually pruned to vase shape.

*Branching habit*.—Upright, crotch angle approximately 30°, increases with heavy crop load.

*Productivity*.—Productive, thinning and spacing necessary for desired market size fruit. Number of fruit set varies with climatic conditions during blooming period.

*Bearer*.—Regular, has had adequate fruit set 4 consecutive years. No alternate bearing observed.

*Fertility*.—Self fertile.

*Density*.—Medium dense, pruning to vase shape desirable for sunlight penetration to center of tree to enhance fruit color and health of fruit wood.

*Hardiness*.—Hardy in all stone fruit growing areas of California. Tree grown in USDA Hardiness Zone 9. Winter chilling requirement approximately 300 hours at or below 45° F.

Trunk:

*Size*.—Large. Average circumference 52.1 cm at 25.4 cm above ground on a 6 year old tree.

*Stocky*.—Medium stocky.

*Texture*.—Medium shaggy, becoming rougher with age.

*Color*.—Varies from 5Y 5/2 to 5Y 4/2.

Branches:

*Size*.—Large. Average circumference 15.0 cm at 1.2 meters above ground. Crotch angle approximately 30°, increases with heavy crop load.

*Surface texture*.—New growth relatively smooth. Mature growth medium rough, roughness increases with age.

*Lenticels*.—Average number 34 in a 25.8 square cm section. Average length 3.9 mm. Average width 1.5 mm. Color varies from 7.5YR 6/12 to 10YR 6/10.

*Color*.—New growth varies from 2.5GY 6/6 to 5GY 5/8. Mature growth varies from 10YR 3/4 to 10YR 3/6, varies with age of growth.

Leaves:

*Size*.—Large. Average length 144.8 mm. Average width 40.4 mm.

*Form*.—Lanceolate.

*Apex*.—Acuminate.

*Base*.—Cuneate.

*Margin*.—Serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 10.3 mm. Average width 1.7 mm. Longitudinally grooved. Surface — glabrous. Color varies from 5GY 4/6 to 5GY 4/8.

*Glands*.—Type — reniform. Size — medium to large. Average length 1.5 mm. Average diameter 1.1 mm. Average number 5, varies from 4 to 6. Located primarily on the base of the leaf blade and the upper portion of the petiole. Color varies from 2.5GY 7/6 to 2.5GY 7/8.

*Stipules*.—Average number 2. Average length 8.1 mm. Edges — pectinate. Color varies from 2.5GY 7/8 to 7.5R 4/10.

*Color*.—Upper surface varies from 5GY 3/6 to 7.5GY 3/6. Lower surface varies from 5GY 4/4 to 5GY 4/6. Midvein varies from 2.5GY 6/6 to 5GY 7/8.

Flower buds:

*Size*.—Medium to large. Average length 12.9 mm. Average diameter 8.5 mm.

*Hardiness*.—Hardy with respect to California winters.

*Density*.—Medium dense.

*Form*.—Conical, becoming elongated just before opening.

*Pedicel*.—Average length 4.8 mm. Average width 1.1 mm. Color varies from 5GY 7/6 to 7.5GY 7/6. Surface glabrous.

*Color*.—Varies from 5RP 7/10 to 7.5RP 6/12.

Flowers:

*Blooming period*.—Date of First Bloom Jan. 27, 2014. Date of Petal Fall Feb. 6, 2014, varies slightly with climatic conditions.

*Size*.—Large, showy. Average height 20.4 mm. Average diameter 39.9 mm.

*Petals*.—Normally 5, alternately arranged to sepals. Size — large. Average length 19.5 mm. Average width 17.4 mm. Form — obovate, narrows at point of attachment. Petal apex — rounded. Petal base —0 acuminate. Arrangement — overlapping. Margin — sinuate. Color varies from 2.5RP 8/6 to 5RP 8/6, fades with age of flower. Both surfaces glabrous.

*Sepals*.—Normally 5, alternately arranged to petals. Size — large. Average length 6.0 mm. Average width 4.9 mm. Shape — ovate, apex rounded. Margin — entire. Surface — upper surface glabrous, lower surface pubescent. Color — upper surface varies from 5GY 5/8 to 5GY 4/8. Lower surface varies from 10R 2/6 to 10R 5/2.

*Stamens*.—Average number 53. Average filament length 15.9 mm. On average, the stamens are below the height of the petals. Filament color N 9.5/(white). Anther color varies from 10R 4/8 to 2.5Y 8/6.

*Pollen*.—Self fertile. Color varies from 5Y 7/12 to 5Y 7/10.

*Pistil*.—Number — normally one. Surface — glabrous. Average length 18.2 mm. Position of stigma an average of 1.0 mm above anthers. Color varies from 10Y 8.5/8 to 7.5Y 8/10.

*Fragrance*.—Slight.

*Color*.—Varies from 2.5RP 8/6 to 5RP 8/6.

*Pedicel*.—Average length 5.4 mm. Average width 1.2 mm. Color varies from 2.5GY 7/6 to 2.5GY 6/8. Surface — glabrous.

*Number flowers per flower bud*.—Normally one.

Fruit: Maturity When Described: Firm ripe and ready for consumption.

*Date of first picking*.—May 11, 2014.

*Date of last picking*.—May 21, 2014, varies slightly with climatic conditions.

*Size*.—Medium to large. Average diameter axially 62.9 mm. Average transversely in suture plane 63.4 mm. Average weight 159.0 grams, varies slightly with fertility of the soil, amount of thinning and climatic conditions.

*Form*.—Globose.

*Suture*.—Slightly lipped.

*Ventral surface*.—Slightly lipped.

*Apex*.—Retuse.

*Base*.—Retuse.

*Stem cavity*.—Rounded to slightly elongated in suture plane. Average depth 5.6 mm. Average diameter 7.2 mm.

Stem:

*Size*.—Small to medium. Average length 8.8 mm. Average diameter 3.1 mm.

*Color*.—Varies from 5GY 6/8 to 5GY 5/8.

Flesh:

*Ripens*.—Evenly.

*Texture*.—Firm, meaty, crisp.

*Fibers*.—Few, small, tender.

*Firmness*.—Firm, comparable to other commercial nectarine varieties.

*Aroma*.—Slight.

*Amydgalin*.—Undetected.

*Eating quality*.—Good.

*Flavor*.—Good, with a good balance between acid and sugar.

*Juice*.—Moderate amount, enhances flavor.

*Acidity*.—Not available.

*Brix*.—Average Brix 11.0°, varies slightly with amount of fruit per tree and climatic conditions.

*Pit cavity*.—Average length 36.2 mm. Average width 26.2 mm. Average depth 12.1 mm. Color 5Y 8/10.

*Color*.—Varies from 2.5Y 8/10 to 5Y 8/10.

Skin:

*Thickness*.—Medium.

*Surface*.—Smooth.

*Pubescence*.—Wanting.

*Tendency to crack*.—None.

*Color*.—Ground color varies from 7.5Y 8/6 to 10Y 8.5/6. Overspread with 5R 2/4 to 7.5R 3/2.

*Tenacity*.—Tenacious to flesh.

*Astringency*.—Undetected.

Stone:

*Type*.—Clingstone, strong adherence to the flesh.

*Size*.—Medium to large. Average length 35.2 mm. Average width 25.2 mm. Average thickness 22.3 mm.

*Form*.—Obovoid.

*Base*.—Flat.

*Apex*.—Round.

*Surface*.—Pitted throughout, pits vary from round to elongated.

*Sides*.—Unequal, one side extending further from suture plane.

*Ridges*.—Small, narrow ridge extending from base toward apex.

*Tendency to split*.—Slight.

*Color*.—Varies from 10YR 7/6 to 10YR 6/6 when dry.

Kernel:

*Size*.—Medium to large. Average length 18.6 mm. Average width 10.7 mm. Average depth 6.7 mm.

*Form*.—Ovoid.

*Viability*.—Non-viable, incomplete embryo development.

*Skin color*.—Varies from 5Y 9/4 to 7.5Y 9/4.

Use: Dessert. Market — local and long distance.

Keeping quality: Good, held firm in cold storage for 2 weeks at 38° to 42° F. without internal breakdown of flesh or appreciable loss of flavor.

Shipping quality: Good, minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of nectarine tree, substantially as illustrated and described.

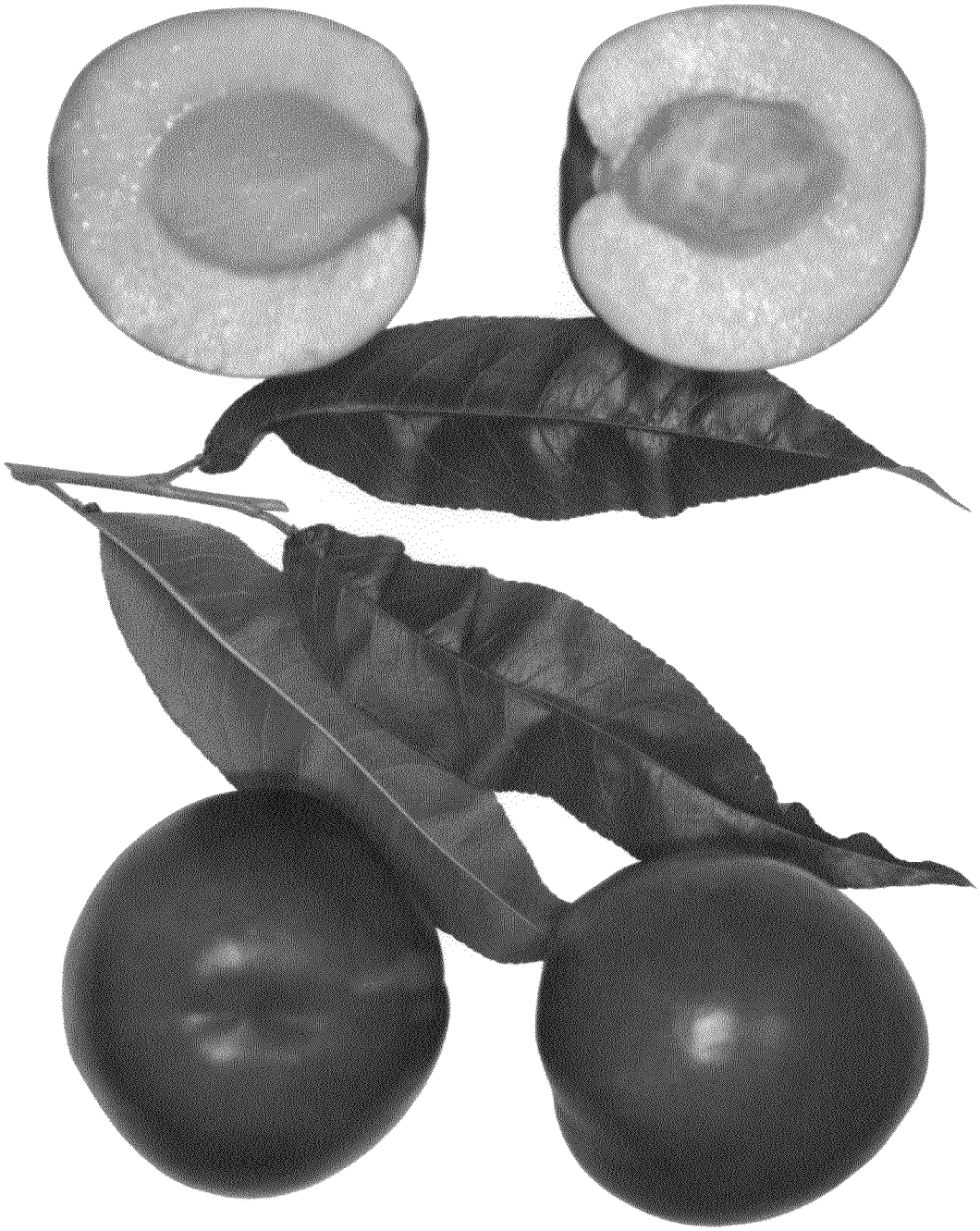

* * * * *